United States Patent [19]

Miyake et al.

[11] 4,124,770
[45] Nov. 7, 1978

[54] SEPARATION OF XYLENOLS FROM CRESOLS WITH ADSORBENT

[75] Inventors: Tetsuya Miyake, Tokyo; Kunihiko Takeda, Yokohama, both of Japan

[73] Assignee: Asahi Kasei Kogyo Kabushiki Kaisha, Osaka, Japan

[21] Appl. No.: 764,129

[22] Filed: Jan. 31, 1977

[30] Foreign Application Priority Data

Feb. 2, 1976 [JP] Japan .................................. 51-9297
Feb. 3, 1976 [JP] Japan .................................. 51-9996

[51] Int. Cl.$^2$ .......................................... C07C 37/24
[52] U.S. Cl. ................................................ 568/758
[58] Field of Search ............ 260/621 B, 621 A, 627 G

[56] References Cited

U.S. PATENT DOCUMENTS

| | | | |
|---|---|---|---|
| 1,830,859 | 11/1931 | Schotte | 260/627 G |
| 2,789,146 | 4/1957 | Neuworth | 260/627 G |
| 3,969,422 | 7/1976 | Neuzil et al. | 260/621 B |

Primary Examiner—James O. Thomas, Jr.
Assistant Examiner—Werren B. Lone
Attorney, Agent, or Firm—Burgess, Dinklage & Sprung

[57] ABSTRACT

A mixture of xylenols and cresols is contacted with a zeolite with aperture of 5.5 Å or more containing at least one cations selected from lithium, potassium, cesium, rubidium, calcium, barium, strontium, cadmium, chromium, molybdenum, manganese, iron, nickel, cobalt, and ammonium to separate xylenols from cresols.

8 Claims, 1 Drawing Figure

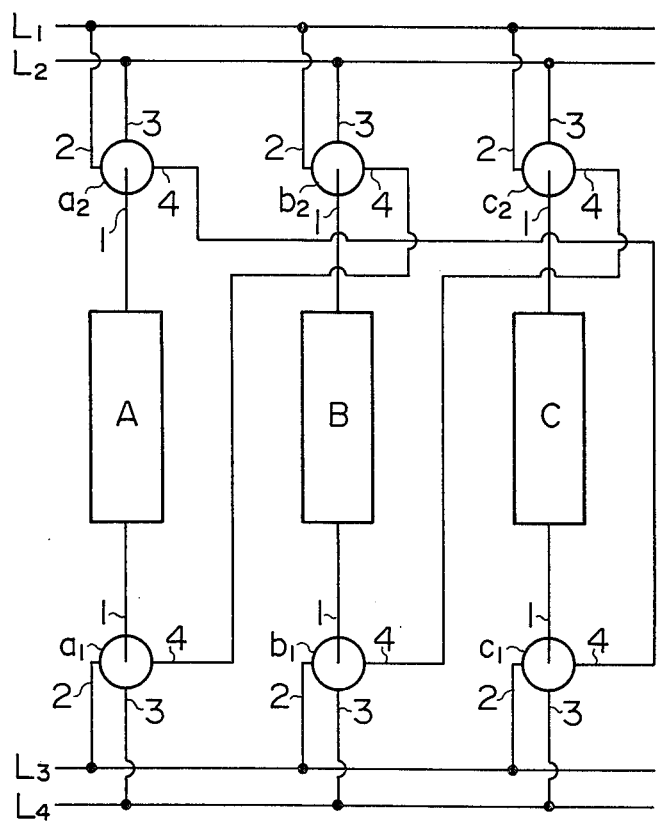

SEPARATION OF XYLENOLS FROM CRESOLS WITH ADSORBENT

This invention relates to a process for separating xylenols from cresols by adsorption method using an adsorbent.

In the art of separation of xylenols from cresols, there have hitherto been known distillation method, reaction separation method or crystallization separation method. Among these, distillation method is not practically available because the boiling points of 2,6-xylenol (202° C.) and 3,5-xylenol (220° C.), which are most useful as industrial chemicals, are close to the boiling point of o-cresol (191° C.), which is often produced with 2,6-xylenol. Moreover, the separation by distillation of 2,6-xylenol and p,m-cresols is impossible (the boiling point of p-cresol and m-cresol are both 202° C.).

On the other hand, 2,4-xylenol cannot be separated from cresol isomers separated by reaction separation method because the chemical reactivity of 2,4-xylenol are similar to that of cresol isomers.

The object of the present invention is therefore to provide a commercially applicable process for separation of xylenols from cresols by adsorption method using an adsorbent.

It has now been found that the above object can be accomplished by using a specifically selected class of adsorbents thereby to effect selective adsorption between xylenols and cresols and thus separate xylenols from cresols. According to the present invention, there is provided a process for separation of xylenols from cresols by adsorption with an adsorbent, which comprises contacting a mixture of xylenols and cresols with an adsorbent comprising a zeolite containing at least one cations selected from the group consisting of lithium, potassium, cesium, rubidium, calcium, barium, strontium, cadium, chromium, molybdenum, manganese, iron, nickel, cobalt, and ammonium, thereby to separate into a stream enriched in xylenols and a stream enriched in cresols. The ratio of said cations based on the total exchangeable cations is preferably 60 mol % or more, most preferably 90 mol % or more.

Among various ions within the scope of the present invention, lithium, potassium, nickel and ammonium are preferred. Several combinations of exchanged ions such as lithium and potassium, lithium and nickel, potassium and nickel, ammonium and lithium, potassium and barium are more preferable when these ions are contained in the zeolite.

The adsorbent to be used in the present invention is found to have desirable ranges of aperture and ratio of silicon to aluminum (Si/Al). In one aspect, the zeolite is desired to have aperture of from 5.5 Å to 15 Å. If a zeolite with aperture of less than 5.5 Å is used, the amount of xylenols and cresols adsorbed is extremely small to be commercially disadvantageous. Further, it is preferred that the ratio of silicon to aluminum in the zeolite is from 0.5 to 4.5. If the ratio exceeds 4.5, the zeolite is reactive with xylenols. With such a zeolite adsorption is practically almost impossible. In other words, the feed material is required to be diluted extremely or development temperature is required to be as low as 40° C. to practical disadvantages. Said ratio of silicon to aluminum is desirably at least 1 in view of the strength of the zeolite.

Typical examples of zeolites to be used in the present invention are type omega ($Na_{6.8}$, $TMA_{16}$ $(Al_2O)_8(SiO_2)_{28}$. 21$H_2O$), natural faujasite, type X($NA_{86}[(AlO_2)_{86}(SiO_2)_{106}]$ 264$H_2O$), type Y($Na_{56}[(AlO_2)_{56}(SiO_2)_{136}].250H_2O$) and type L($K_9[(AlO_2)_9(SiO_2)_{27}]$ 22$H_2O$). Among them, type X and type Y zeolites are particularly preferred. While naturally occurring products are available, these zeolites can also be produced by well-known synthetic methods, as disclosed by Japanese Patent Publication Nos. 6712/57, 18267/60, 1639/61 and 124/63.

The zeolites to be used in the present invention are required to have exchangeable cationic sites exchanged totally or partially by at least one of a specific group of cations, namely lithium, potassium, cesium, rubidium, calcium, barium, strontium, cadmium, chromium, molybdenum, manganese, iron, nickel, cobalt and ammonium. Among them, preferable class of zeolites are those wherein the exchanged cations are lithium, potassium, nickel, ammonium or combination thereof.

Typical adsorbents of the present invention can be produced by using type faujasite zeolites as starting material and subjecting them to ion exchange. The type faujasite zeolites used as the starting material belong to group 4, i.e. "double 6 ring", according to classification of crystalline structures among crystalline aluminosilicates which are generally called zeolites. The group 4 encompass zeolites of the types faujasite, chabasite, gmelinite and ZK-5.L. The faujasite is characterized by the polyhedral cage type, $\beta$, 26-hedron. The faujasites include, other than natural faujasite, type X synthetic zeolites and type Y zeolites. The type X zeolites can be represented in terms of the mole oxides for the sodium form as represented by the formula: $Na_2O.Al_2O_3.2.5SiO_2.6H_2O$ and in terms of unit cell parameters for $Na_{86}[(AlO_2)_{86}(SiO)_{106}].264H_2O$, density: 1.93 g/cc; unit cell constant: 25.02–24.86 Å; void volume: 0.50 cc/cc; aperture: 12 ring 7.4 Å, 6 ring 2.2 Å; and kinetic aperture: 8.1 Å. Y type zeolites can be represented in terms of the mole oxides for the sodium form as represented by the formula: $Na_2O.Al_2O_3.4.8SiO_2.8.9H_2O$ and in terms of unit cell parameters: for $Na_{56}[(AlO_2)_{56}(SiO_2)_{136}].250H_2O$, density: 1.92 g/cc; unit cell constant: 24.85–24.61 Å; void volume: 0.48 cc/cc; aperture: 12 ring 7.4 Å, 6 ring 2.2 Å; kinetic aperture: 8.1 Å. The sodium in the above oxides representation occurs since it is used at the time of synthesis of zeolites for convenience in synthesis. After formation of crystals, sodium ions can be exchanged with other cations such as alkali metal ions.

Exchange of cations can be effected by contacting the starting material with an aqueous solution of soluble salts of the cations to be exchanged. As such salts, there may generally be used chlorides, nitrates, sulfates and carbonates. The absolute amount of cations contained in the solution is desirably at least 0.8 times as much as the equivalent amount in the type faujasite zeolite to be exchanged. The solution used for ion exchange has a concentration of salt from 0.01 wt.% to saturation, desirably from 5 to 20 wt.%. While the ion exchange is operable at a temperature of from 2° to 98° C., it is preferably conducted at a relatively high temperature for rearrangement of crystal structure and acceleration of ion exchange.

According to a preferable method, the starting material is first converted to the form of ammonium, followed by conversion into hydrogen form by calcination, and then exchanged with desired cations. The details of this method are disclosed by Japanese Patent Publication Nos. 6713/57, 618/58 and 5523/58.

The original cations in the starting material are usually sodium form. The amount of sodium ions remained after ion exchange is desired to be lowered to about 10 wt.% or less.

The type faujasite zeolite which has been subjected to ion exchange according to the above procedures is usually dried to appropriate water content by means of vacuum drying, freeze-drying, hot air drying or electric furnace drying before it is provided for use. The ratio of constituting elements, the ratio of constituting cations and the exchange ratio are confirmed by elemental analyzer and the crystalline structure by X-ray diffraction spectrometer before the adsorbent is put to use.

The adsorbent of the present invention can be used in various shapes, namely solely with sizes of 2 microns or more, or in pellets together with about 20% inorganic binders (e.g. Kaolinite or bentonite) of up to ⅛ inch. For acceleration of ion exchange speed or absorption-desorption speed, the particles sizes of the adsorbent are desirably as small as possible. On the other hand, from standpoint of operation technique, it is desired to use adsorbent shaped in particle with larger particle size or adsorbent shaped in pellet for the purpose of decreasing pressure drop to make the operation easier.

The mixture of xylenols and cresols to be separated in the present invention includes mixtures of at least one xylenol and at least one cresol. The cresols herein contemplated encompass all isomers, namely o-cresol, m-cresol and p-cresol. Likewise, xylenols include all isomers as represented by the position of methyl groups, i.e. (2,6), (2,3), (2,4), (2,5), (3,4), (3,5), (3,6), (4,5), (4,6), and (5,6). Typical examples of the feed mixture for which the present invention can suitably be applied are a mixture of 2,6-xylenol and o-cresol, a mixture of 3,5-xylenol and m-cresol and a mixture of 2,6-xylenol, p-cresol and m-cresol. The mixture may further contain other substances such as phenol; alkyl phenols, e.g. trimethyl phenol isomers, tert-butyl cresol isomers, di-tert-butyl cresol isomers, $\alpha$-naphtol, $\beta$-naphthol, ethylphenol, carvacrol, thymol, phenylphenol, benzyl-phenol, pyrocatechin, pentadecyl catechol, guaiacol, cresol, eugenol, iso-eugenol; and halogen phenols. The composition of the mixture is not limited but may vary widely and presence of third components is also admissible.

Various adsorption-desorption operational procedures are known in the art of adsorption separation method. The basic unit operation is to adsorb preferentially components having stronger adsorbing power among the substances to be separated and recover components having weaker adsorbing power earlier. The simplest procedure is so called batch process wherein the substance to be separated is fed to an adsorption bed packed with adsorbents and a stream enriched in components having weaker adsorbing power is recovered earlier and more strongly adsorptive components are thereafter recovered thermally or by use of a desorbent. A wide range of desorbents having various properties can be used in this procedure. Continuous separation methods are also known as improved methods. These methods are generally conducted by eluting or displacing the mixture of xylenols and cresols adsorbed on a bed of adsorbents with an eluant or displacement agent through said bed of adsorbents thereby to further effect separation and recover separated fractions. According to one method, eluant is circulated through the adsorption bed while passing the substances to be separated and separation is effected through interaction between the development agent and the adsorbent. The other method comprises using displacement agent which displaces the adsorption zone of the substance to be separated, formed in the adsorbent bed, substantially without passing said substance, whereby separation is effected by the action of the adsorbent.

The development agents (eluant or displacement agent) suitably used in this invention are polar compounds, such as alcohols, ketones, amides, amines, ethers, esters, nitrils, nitro-compounds, halogenated hydrocarbons and sulfur compounds. For example, ethanol, n-propyl alcohol, n-butyl alcohol, iso-butyl alcohol, sec-butyl alcohol, n-amyl alcohol, n-octanol, cyclohexanol; acetone, methylethylketone, diethylketone, acetophenone, cyclohexanone, propionitril, butyronitril, 1-nitropropane, ethylenediamine, methylenechloride and dimethylsulfone are preferably used.

According to the preferred embodiment of the present invention, a development agent selected from the group of ketones and alcohols is used.

When a development agent is used, the process can be practiced by first feeding the material to be separated to a bed of adsorbents to form adsorption zone of said material and then feeding development agent to said bed in contact with said adsorption zone to displace said zone. As the progress of development, strongly adsorptive components are enriched in the rear end of the adsorption zone and the development agent and weakly adsorptive components are enriched in the forefront of the adsorption zone. When the compositions at these portions of the adsorption zone reach desired values, they can be removed from the bed as product streams, respectively. In practicing this embodiment, development agent can be filled in the bed before feeding the material to be separated thereby to form another boundary at forefront of the adsorption zone. The process can be practiced by use of either single or plural columns connected in parallel or in series. In particular, continuous operation by use of plural columns connected in series in a closed recycle system is recommendable. In continuous operation, when the adsorbed material to be separated is decreased due to intermittent or continuous removal of separated fractions, fresh feed material is supplemented to the adsorption zone at the central portion thereof.

Referring now to the accompanying drawing, FIG. 1 shows flow-sheet of one typical arrangement of the apparatus for practicing the above embodiment of the present invention by continuous operation, three development columns A, B and C are employed. In said drawing, each of $a_1$, $a_2$, $b_1$, $b_2$, $c_1$ and $c_2$ shows four-channel exchange valve, in which the numbers 1 to 4 designates exchange channels; $L_1$, $L_2$, $L_3$, and $L_4$ shows principal pipes. For the convenience of explanation, each of the columns A, B and C is packed with adsorbents and filled with development agent. Furthermore, the mixture of xylenols and cresols is now under separation by development in the column A and there exists in the middle portion of the column A a region wherein the material to be separated and the development agent are mixed. Under this state, the exchange valve $a_1$ for the column A is opened in the direction (1-3) and the development agent is fed through the route $L_4$-$a_1$(3-1)-A from the bottom of the column A. The adsorption zone of the material to be separated is formed and, while being separated, said adsorption moves upward gradually through the column A. When the forefront of the material to be separated reaches top of the column, the fractions with desired composition at the frontal portion (hereinafter referred to merely as front cut) are recovered continuously or intermittently through the route A-$a_2$(1-2)-$L_1$. After recovery of the front cut, the remainder of the material to be separated which has not yet been separated in the column A is transferred by opening the exchange valve $a_2$ in the direction of (1-4) through the route A-$a_2$(1-4)-$c_1$(4-1)-C into the column C. In the course of transfer, when about half of the remainder of the material has been transferred into the column C, the four-channel exchange valve $c_1$ is opened to permit introduction of fresh feed material to be separated in predetermined amount through the route $L_3$-$c_1$(2-1)-C in to the column C. The amount of the material newly fed is adjusted to approximately equal to that of the front cut recovered from the column A. After the supplemental feed has been completed, the residual part of the material in the column A is transferred into the column C. When the fractions with desired composition in the rear-end portion of the adsorption zone (hereinafter referred to merely as rear cut) reach the top of the column A, they are recovered through the route A-$a_2$(1-2)-$L_2$. Feeding of the development agent is continued through the route $L_4$-$c_1$(3-1)-C to further continue development. When the newly separated front cut reaches top of the column C, it is recovered through the route C-$c_2$(1-2)-$L_1$ and the remainder which has not yet been separated is transferred into the column B through the route C-$c_2$(1-4)-$b_1$(4-1)-B by opening the four-channel exchange valve $c_2$ in the direction of (1-4) into the column B. Following the procedures, as described above, between the columns A and C, front cut and rear cut are recovered from the top of the column B, respectively. Thus, by circulating a part of the material to be separated through the closed loop, i.e. A—C—B—A ... . while continuing feed of the supplemental material to be separated and the development agent and using the adsorbent in continuous operation, fractions with desired composition can be successively recovered from each column. As apparently seen from the above explanation, use of three columns is not essential for continuous operation but operation by use of two columns in the least is possible. Four or more columns are of course available.

In the present invention, adsorption is conducted at a temperature from about 20° to 320° C., preferably from 30° to 220° C. under a pressure from atmospheric pressure to 50 ata., preferably from atmospheric pressure to about 30 ata. The adsorption step may be carried out in either liquid or gaseous phase. For the purpose of operation at a lower temperature, liquid phase operation is preferred. The development can also be conducted under similar conditions; but the conditions may be varied to lower pressure or elevated temperature or both. Preferably, the adsorption and development are carried out at the same temperature and in liquid phase.

The present invention is illustrated in further detail by referring to the following Examples:

EXAMPLE 1

In this Example, various adsorbents including both type X and type Y zeolites as set forth in Table 1 are used. A mixture of 80 wt.% of 2,6-xylenol and 20 wt.% of p-cresol is fed into a laboratory glass column packed with each adsorbent. Said column is 2 cm in diameter and 50 cm in length, cylindrical in shape and equipped with a jacket. Feeding is continued at a temperature maintained at 140° C. for 4 hours, until 10 liter of the feed is flown through the column. Subsequently, the non-adsorbed fractions are purged with nitrogen gas and the adsorbed fractions are desorbed with 2 liters of methyl alcohol. The desorbed fractions are subjected to analysis. The adsorbent is dried before being weighed, whereby it is confirmed that there is no residual adsorbed substance on the adsorbent. Selectivity coefficients measured for respective type X and type Y zeolites are set forth in Table 1.

Table 1

| Ionic species | | | Composition of ions (mol. %) | | Selectivity coefficient | |
|---|---|---|---|---|---|---|
| First ion | Second ion | | First ion | Second ion | (type X) | (type Y) |
| Sodium | — | (Control) | 100 | 0 | 2.8 | 2.5 |
| Lithium | Sodium | | 95 | 5 | 10.3 | 9.2 |
| Potassium | Sodium | | 97 | 3 | 10.7 | 9.6 |
| Rubidium | Sodium | | 68 | 32 | 5.4 | 4.5 |
| Cesium | Sodium | | 65 | 35 | 4.9 | 3.6 |
| Strontium | Sodium | | 82 | 18 | 4.6 | 3.4 |
| Cadmium | Sodium | | 65 | 35 | 4.5 | 4.3 |
| Barium | Sodium | | 66 | 34 | 4.8 | 3.7 |
| Chromium | Sodium | | 65 | 35 | 4.5 | 3.6 |
| Molybdenum | Sodium | | 66 | 34 | 4.8 | 5.9 |
| Manganese | Sodium | | 66 | 34 | 5.6 | 3.5 |
| Iron | Sodium | | 68 | 32 | 5.4 | 4.8 |
| Nickel | Sodium | | 93 | 7 | 11.2 | 9.5 |
| Cobalt | Sodium | | 68 | 32 | 6.8 | 5.5 |
| Ammonium | Sodium | | 91 | 9 | 10.8 | 9.4 |
| Lithium | Potassium | | 39 | 61 | 12.6 | 11.5 |
| Lithium | Nickel | | 45 | 55 | 12.3 | 11.1 |
| Potassium | Nickel | | 81 | 19 | 13.6 | 12.3 |
| Ammonium | Lithium | | 24 | 76 | 13.3 | 11.6 |
| Potassium | Barium | | 82 | 18 | 11.3 | 10.5 |
| Lithium | Cobalt | | 92 | 8 | 10.5 | 10.6 |
| Lithium | Cesium | | 61 | 39 | 10.7 | 8.9 |
| Potassium | Magnesium | | 82 | 18 | 10.9 | 8.1 |
| Lithium | Calcium | | 43 | 57 | 10.1 | 9.6 |

Note) Selectivity coefficient $K_a^b$ is represented by formula:

$$K_a^b = \frac{\left(\frac{\text{mole fraction of b adsorbed}}{\text{mole fraction of a adsorbed}}\right)}{\left(\frac{\text{mole fraction of b in equilibrated liquid}}{\text{mole fraction of a in equilibrated liquid}}\right)}$$

wherein a is xylenol and b is cresol.

EXAMPLE 2

In this Example, various development agents are tested by using an adsorption chamber made of pyrex glass tube of 4 m in length and 0.8 cm in diameter packed with 200 cc of adsorbents. This glass column is maintained at about 100° C. Gaschromatograph analyzer is equipped at the outlet for effluent from the column to determine the composition of the effluent, by which selectivity is measured.

First, the development agent is fed into the column at the rate of 8.75 cc/minute. Then, flow of the development agent is discontinued and the material to be separated is fed at the same rate for 20 minutes. Subsequently, the development agent is fed again at the rate of 8.75 cc/minute into the column until whole of the material to be separated is eluted out of the column. The feed material to be separated and the adsorbent is varied as shown in Table 2. The results are also shown in Table 2.

Table 2

| Run No. | Type of zeolite | Feed material (wt. %) | Development agent | Front cut (wt. %) | | Rear cut (wt. %) | |
|---|---|---|---|---|---|---|---|
| 1 | Y | o-cresol | ethyl | o-cresol | (1.7) | o-cresol | (90.6) |

Table 2-continued

| Run No. | Type of zeolite | Feed material (wt. %) | Development agent | Front cut (wt. %) | | Rear cut (wt. %) | |
|---|---|---|---|---|---|---|---|
| | (lithium) | 2,6-xylenol (20) (80) | alcohol | 2,6-xylenol | | 2,6-xylenol | (9.4) |
| 2 | " | " | iso-propyl alcohol | o-cresol 2,6-xylenol | (0.4) (99.6) | o-cresol 2,6-xylenol | (93.1) (6.9) |
| 3 | " | " | n-butyl alcohol | o-cresol 2,6-xylenol | (0.2) (99.8) | o-cresol 2,6-xylenol | (98.9) (1.1) |
| 4 | " | " | iso-amyl alcohol | o-cresol 2,6-xylenol | (0.2) (99.8) | o-cresol 2,6-xylenol | (98.2) (1.8) |
| 5 | " | " | n-hexyl alcohol | o-cresol 2,6-xylenol | (0.3) (99.7) | o-cresol 2,6-xylenol | (97.3) (2.7) |
| 6 | " | " | n-octyl alcohol | o-cresol 2,6-xylenol | (3.8) (96.2) | o-cresol 2,6-xylenol | (90.1) (9.9) |
| 7 | " | " | cyclohexyl alcohol | o-cresol 2,6-phenol | (22.7) (77.3) | o-cresol 2,6-phenol | (71.5) (28.5) |
| 8 | Y (sodium potassium) | " | n-butyl alcohol | o-cresol 2,6-xylenol | (0.1) (99.9) | o-cresol 2,6-xylenol | (99.1) (0.9) |
| 9 | " | o-cresol (5) m-cresol (5) p-cresol (5) phenol (5) 2,6-xylenol (80) | " | o-cresol m-cresol p-cresol phenol 2,6-xylenol | (0.05) (0.03) (0.01) (0.01) (99.90) | o-cresol m-cresol p-cresol phenol 2,6-xylenol | (22.3) (24.6) (24.9) (28.1) (0.1) |
| 10 | X (nickel form) | p-cresol 2,6-xylenol (40) (60) | 2-butanol | p-cresol 2,6-xylenol | (0.1) (99.9) | p-cresol 2,6-xylenol | (99.8) (0.2) |
| 11 | " | " | methyl ethyl ketone | p-cresol 2,6-xylenol | (0.2) (99.8) | p-cresol 2,6-xylenol | (99.8) (0.2) |
| 12 | " | p-cresol 2,6-xylenol (40) (60) | butyronitril | p-cresol 2,6-xylenol | (0.02) (99.98) | p-cresol 2,6-xylenol | (99.9) (0.1) |
| 13 | " | " | 1-nitropropane | p-cresol 2,6-xylenol | (0.3) (99.7) | p-cresol 2,6-xylenol | (99.6) (0.4) |
| 14 | " | m-cresol 3,5-xylenol (10) (90) | 2-butanol | m-cresol 3,5-xylenol | (0.4) (99.6) | m-cresol 3,5-xylenol | (99.4) (0.6) |
| 15 | " | " | methyl ethyl ketone | m-cresol 3,5-xylenol | (1.1) (98.9) | m-cresol 3,5-xylenol | (99.0) (1.0) |
| 16 | " | " | butyronitril | m-cresol 3,5-xylenol | (0.3) (99.7) | m-cresol 3,5-xylenol | (99.4) (0.6) |
| 17 | " | " | 1-nitropropane | m-cresol 3,5-xylenol | (2.3) (97.7) | m-cresol 3,5-xylenol | (88.4) (12.6) |

What we claim is:

1. A process for separating xylenols from cresols, comprising the following steps:
   (a) feeding a mixture of xylenols and cresols to a column containing a zeolite having apertures of from 5.5 to 15 Å and containing at least one cation selected from the group consisting of lithium, potassium, cesium, rubidium, calcium, barium, strontium cadmium, chromium, molybdenum, manganese, iron, nickel, cobalt and ammonium,
   (b) feeding a development agent through said column at a temperature from 20° to 320° C. under a pressure from atmospheric to 50 ata., thereby preferentially to dislodge xylenol molecules from the column whereby the concentration of xylenols is increased in the development agent first coming through said column and the concentration of cresols is increased in the development agent later coming through said column, said development agent being selected from the group consisting of ethanol, n-propyl alcohol, n-butyl alcohol, isobutyl alcohol, sec-butyl alcohol, n-amyl alcohol, n-octanol, cyclohexanol, acetone, methylethylketone, diethylketone, acetophenone, cyclohexanone, propionitrile, butyronitrile, 1-nitropropane, ethylenediamine, methylenechloride and dimethylsulfone, and
   (c) recovering a fraction of development agent enriched in xylenols from the effluent from the column.

2. A process as in claim 1, wherein the zeolite has a ratio of silicon to aluminum (Si/Al) of from 0.5 to 4.5.

3. A process as in claim 1, wherein the zeolite contains at least one of lithium, potassium, nickel and ammonium.

4. A process as in claim 1, wherein 90 mol.% or more of the cationic sites are exchanged with at least one cation as defined in claim 1.

5. A process as in claim 1, wherein the zeolite contains one combination of cations selected from the group consisting of lithium-potassium, lithium-nickel, potassium-nickel, ammonium-lithium and potassium-barium.

6. A process as in claim 1, wherein the mixture of xylenols and cresols adsorbed on a bed of adsorbents is eluted or developed with a development agent through said bed of adsorbents thereby to further effect separation and recover separated fractions.

7. A process as in claim 1, wherein separation is operated by use of plural columns packed with the adsorbents and connected in series in a closed recycle system by forming an adsorption zone of xylenols and cresols and developing said zone through said plural columns, and recovering a stream enriched in xylenols from the forefront portion of said adsorption zone and a stream enriched in cresols from the rear-end portion of said adsorption zone, respectively, intermittently or continuously.

8. A process as in claim 7, wherein fresh feed of a mixture containing xylenols and cresols is charged supplementarily to the central portion of the adsorption zone, intermittently or continuously.

* * * * *